US009642573B2

(12) United States Patent
Zhao et al.

(10) Patent No.: US 9,642,573 B2
(45) Date of Patent: *May 9, 2017

(54) PRACTITIONER DEVICE FOR FACILITATING TESTING AND TREATMENT OF AUDITORY DISORDERS

(71) Applicants: Yong D Zhao, Simi Valley, CA (US); Jennifer Jinping Zhao, Simi Valley, CA (US)

(72) Inventors: Yong D Zhao, Simi Valley, CA (US); Jennifer Jinping Zhao, Simi Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/884,365

(22) Filed: Oct. 15, 2015

(65) Prior Publication Data
US 2017/0071534 A1 Mar. 16, 2017

Related U.S. Application Data

(63) Continuation-in-part of application No. 14/855,835, filed on Sep. 16, 2015.

(51) Int. Cl.
H04R 25/00 (2006.01)
A61B 5/00 (2006.01)
A61B 5/12 (2006.01)
A61F 11/00 (2006.01)
A61B 5/16 (2006.01)
(Continued)

(52) U.S. Cl.
CPC ............ A61B 5/4836 (2013.01); A61B 1/227 (2013.01); A61B 5/0004 (2013.01); A61B 5/0476 (2013.01); A61B 5/123 (2013.01); A61B 5/126 (2013.01); A61B 5/128 (2013.01); A61B 5/165 (2013.01); A61B 5/168 (2013.01); A61B 5/4806 (2013.01); A61B 5/4884 (2013.01); A61B 5/6898 (2013.01); A61B 5/7475 (2013.01); A61F 11/00 (2013.01); A61M 21/02 (2013.01); H04R 25/554 (2013.01); A61B 2560/0475 (2013.01); A61M 2021/0027 (2013.01)

(58) Field of Classification Search
CPC ........ H04R 29/00; H04R 25/00; H04R 25/55; H04R 25/558
USPC ............................................ 381/60, 312–315
See application file for complete search history.

(56) References Cited

U.S. PATENT DOCUMENTS 7,779,153 B2 * 8/2010 Van den Heuvel ............. A61N 1/36032
381/60
7,965,851 B2 * 6/2011 Bengtsson ........... A61B 5/0002
381/60
(Continued)

Primary Examiner — Suhan Ni

(57) ABSTRACT

A practitioner device for facilitating at least one of testing and treatment of at least one auditory disorder is disclosed. The practitioner device includes a user interface configured for receiving an input from a practitioner. Further, the practitioner device includes a communication interface configured for communicating information between the practitioner device and at least one of a mobile device and another practitioner device over at least one of a wired communication channel and a wireless communication channel, wherein the information is based on the input, wherein the information corresponds to at least one of at least one auditory test and at least one auditory treatment procedure, wherein the mobile device facilitates at least one of testing of at least one auditory disorder and treatment of at least one auditory disorder.

20 Claims, 6 Drawing Sheets

(51) Int. Cl.
*A61M 21/02* (2006.01)
*A61B 5/0476* (2006.01)
*A61B 1/227* (2006.01)
*A61M 21/00* (2006.01)

(56) References Cited

U.S. PATENT DOCUMENTS 8,300,840 B1 * 10/2012 Frye ............. H04R 29/00
    381/313
8,798,295 B2 * 8/2014 Menzl et al. .......... H04R 25/70
    381/314

* cited by examiner

PRACTITIONER DEVICE FOR FACILITATING TESTING AND TREATMENT OF AUDITORY DISORDERS

The current application is a continuation in part of U.S. patent application Ser. No. 14/855,835 filed Sep. 16, 2015.

FIELD OF THE INVENTION

The present invention generally relates to electronic devices. More particularly, the present invention relates to methods, systems and apparatus for facilitating testing and treatment of auditory disorders including, but not limited to, tinnitus, sound sensitivity disorder, misophonia, hyperacusis, insomnia, stress, depression, hyperactivity, anxiety and hearing loss.

BACKGROUND

Tinnitus is a physical condition, experienced as an aural perception of noise when no such external physical noise is present. Most often, in patients suffering from tinnitus, this noise presents itself as a ringing in the ears. In other cases, patients describe hearing other sounds such as a hissing, clicking or roaring noise in the ears, in the absence of external stimuli.

Testing and treating tinnitus is a difficult task because of its inherent variability. For instance, patients may not experience the same level of tinnitus in both ears. Additionally, factors such as the time of the day and environment, may affect the ways in which tinnitus presents itself. Moreover, tinnitus often causes psychological effects such as, elevated stress and anxiety, due to the persistence of the noise. Long-term auditory nerve damage is yet another consequence of leaving tinnitus untreated. Many patients suffering from tinnitus also report hearing loss over time.

Patients experiencing tinnitus currently do not receive round the clock clinical care. Treatment involves visiting hospitals and consulting experts, to fine tune tinnitus treatment devices.

Therefore, there is a need for methods, systems and apparatus that may facilitate testing and treating auditory disorders such as, but not limited to, tinnitus and hearing loss. Further, there is need for methods, systems and apparatus that may allow a patient to receive care for testing and treating auditory disorders when the patient is away from the hospital. Additionally, for auditory disorders with high levels of variability, there is a need for methods, systems and apparatus that may allow rapid adjustment of auditory treatment, in response to changes in the symptoms of the auditory disorder affecting the patient.

SUMMARY

A practitioner device for facilitating at least one of testing and treatment of at least one auditory disorder is disclosed according to some embodiments. The practitioner device includes a user interface configured for receiving an input from a practitioner. Further, the practitioner device includes a communication interface configured for communicating information between the practitioner device and at least one of a mobile device and another practitioner device over at least one of a wired communication channel and a wireless communication channel, wherein the information is based on the input, wherein the information corresponds to at least one of at least one auditory test and at least one auditory treatment procedure, wherein the mobile device facilitates at least one of testing of at least one auditory disorder and treatment of at least one auditory disorder.

A method for facilitating at least one of testing and treatment of at least one auditory disorder is disclosed according to some embodiments. The method includes receiving, through a user interface of a practitioner device, an input from a practitioner. Thereafter the method includes communicating, through a communication interface of the practitioner device, information between the practitioner device and at least one of a mobile device and another practitioner device over at least one of a wired communication channel and a wireless communication channel, wherein the information is based on the input, wherein the information corresponds to at least one of at least one auditory test and at least one auditory treatment procedure, wherein the mobile device facilitates at least one of testing of at least one auditory disorder and treatment of at least one auditory disorder.

DESCRIPTION

Figure 1:
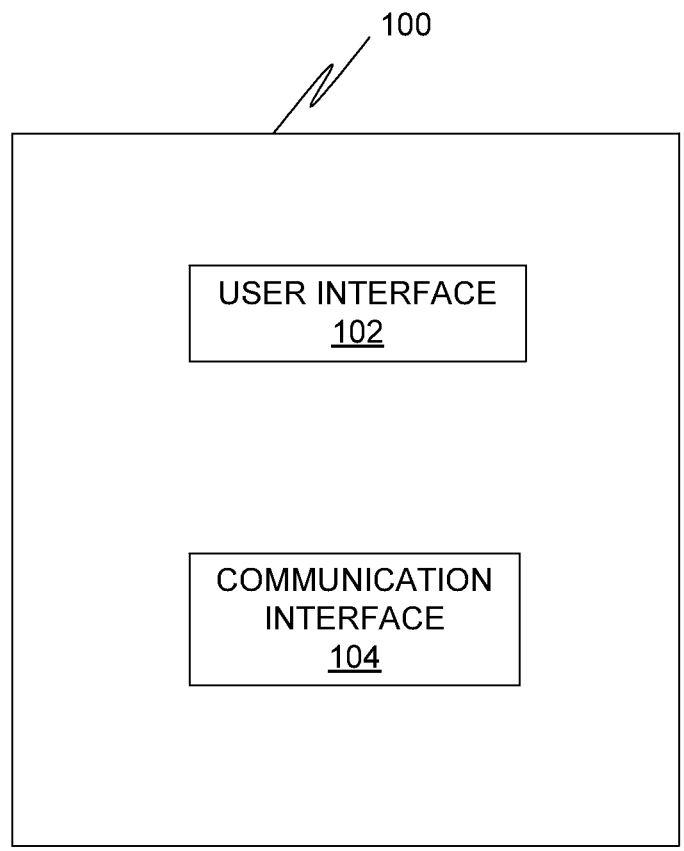
FIG. 1 illustrates a practitioner device for facilitating one or more of testing and treatment of an auditory disorder, in accordance with an embodiment.

The following detailed description is provided with reference to the figures. Exemplary, and in some case preferred, embodiments are described to illustrate the disclosure, not to limit its scope, which is defined by the claims. Those of ordinary skill in the art will recognize a number of equivalent variations in the description that follows.

Disclosed herein is a practitioner device for facilitating testing and treatment of an auditory disorder. The practitioner device may operate in conjunction with a mobile device for performing one or more of, an auditory test and an auditory treatment procedure. The auditory disorder may include one or more of, but not limited to, tinnitus, hearing loss, sound sensitivity, hyperacusis, misophonia, insomnia, stress, depression, hyperactivity, and anxiety.

The practitioner device may be one or more of, but not limited to, a personal mobile smart phone, a telephone, a personal digital assistant, an email device, a laptop computer, a desktop computer, a tablet, a hearing aid and an MP3 player. Additionally, the practitioner device may be an integrated microelectronic device capable of facilitating testing and treatment of the auditory disorder.

In an embodiment, the practitioner device may operate in conjunction with the remote mobile device for testing and treating the auditory disorder. Alternatively, in another embodiment, the practitioner device may be a stand-alone device capable of administering testing and treatment for the auditory disorder. Additionally, a user of the practitioner device may be one or more of, but not limited to, a clinical expert and a doctor.

The practitioner device may facilitate performing the auditory test such as one or more of, but not limited to, a hearing loss test, a tinnitus sound matching and capturing test, a sound sensitivity disorder (SSD) test, a hyperacusis test, a misophonia test, an insomnia test, a stress test, a depression test, a hyperactivity test, an anxiety test and a relaxation test. Further, at least one of the practitioner device and the mobile device may generate a sound signal for treating the auditory disorder. Moreover, the sound signal generated may simulate an acoustic characteristic of a physical environment where the user has experienced a symptom corresponding to the auditory disorder. For example, the user may have experienced a tinnitus sound while in a restaurant. Accordingly, the sound signal generated may simulate the background sound of a restaurant that may include sounds of several people talking.

A hearing loss test may be conducted using at least one of the practitioner device and the mobile device to generate acoustic waves, and measuring the response of the user to the acoustic waves. Accordingly, at least one of the practitioner device and the mobile device may be configured for receiving a response through a user interface of the at least one of the practitioner device and the mobile device. The user interface of the at least one of the practitioner device and the mobile device may be one or more of, but not limited to, knobs, dials, buttons, touch sensitive screens, volume controls, keyboards, pointers, mouse and touch pads. The response may be representative of the aural perception of the user to the auditory stimuli presented. Additionally, conducting the hearing loss test may also include varying the characteristics of the acoustic waves such as, one or more of, but not limited to, a frequency and intensity. Additionally, the threshold of the intensity at each frequency may be progressively reduced to identify the least intensity that the user may hear.

In an instance, at least one of the practitioner device and the mobile device may also perform a tinnitus sound matching and capturing test, by generating and varying the parameters of acoustic waves until, an acoustic wave that best matches a target tinnitus sound may be identified. Further, the target tinnitus sound may be a sound that a user suffering from tinnitus, hears persistently. In an instance, the at least one of the practitioner device and the mobile device may be configured for selecting an acoustic wave from a library of acoustic waves to be administered to the user. In another embodiment, the at least one of the practitioner device and the mobile device may be configured for synthesizing the acoustic waves based on a set of parameters identified as suitable for matching and capturing the target tinnitus sound. In yet another embodiment, the at least one of the practitioner device and the mobile device may also be configured for receiving an input from the user representing an aural perception of the user to the sound presented, through the user interface. For instance, the at least one of the practitioner device and the mobile device may present a first set of acoustic waves and a second set of acoustic waves to the user in succession. Thereafter, the user may be asked to identify whether the first set of acoustic waves or the second set of acoustic waves, is closer to the target tinnitus sound.

Similarly, the at least one of the practitioner device and the mobile device may also administer the auditory test for SSD. Further, types of SSD such as one or more of, but not limited to, misophonia and hyperacusis, may also be tested. A user suffering from misophonia may be unable to withstand acoustic waves of a particular pattern, such as, but not limited to, the sound of slurping, nail clicking and throat clearing. Whereas, hyperacusis refers to noise sensitivity to a certain range of parameters of acoustic waves. For example, users suffering from hyperacusis may be unable to withstand acoustic waves corresponding to a certain range of frequency. The at least one of the practitioner device and the mobile device may be able to administer both subjective and objective tests for identifying misophonia and hyperacusis. For example, the at least one of the practitioner device and the mobile device may conduct the hyperacusis test by varying the level of a parameter of the acoustic waves generated, for identifying a range of the parameter that the user is unable to tolerate. The at least one of the practitioner device and the mobile device may perform the misophonia test by asking the user to provide information about user's perceived tolerance levels to certain specific sound patterns of acoustic waves, generated by the at least one of the practitioner device and the mobile device.

Additionally, the at least one of the practitioner device and the mobile device may be configured to facilitate performing of an auditory treatment procedure such as, but not limited to, Acoustic Tinnitus Masking Therapy (ATMT), Acoustic Tinnitus Retraining Therapy (ATRT), Acoustic Tinnitus Stimulation Therapy (ATST), Cognitive Habituation Tinnitus Therapy (CHaTT), Acoustic Insomnia Therapy (AIT), Acoustic Stress Therapy (AST), Acoustic Depression Therapy (ADT), Acoustic Hyperactivity Therapy (AHT), Acoustic Anxiety Therapy (AAT) and Acoustic Relaxation Therapy (ART). In some embodiments, the auditory treatment procedure is based on one or more of habituation, suppression, distraction, attention diversion, relaxation, positive association and neuromodulation.

In an instance, the at least one of the practitioner device and the mobile device may facilitate performing a passive auditory treatment procedure such as one or more of, but not limited to, ATRT and ATMT. Additionally performing ATRT and ATMT involves, utilizing a combination of sound therapy and psychological counselling for providing relief to the user. Sound therapy may involve, generating acoustic waves of a therapeutic nature for masking noises associated with the auditory disorder. Similarly, the at least one of the practitioner device and the mobile device may also be capable of facilitating performing an active auditory treatment procedure such as, but not limited to, ATST. Administering ATST may involve, generating acoustic waves to be used in inhibiting the spontaneous excitement of auditory neurons. The at least one of the practitioner device and the mobile device may facilitate administering ATST by delivering acoustic waves to the ear. The acoustic waves delivered may induce depolarization of auditory neurons, leading to de-sensitization of the auditory nerve. Reducing the sensitivity of the auditory nerve may in turn, lead to reducing the generation of false noises, perceived as the targeted tinnitus sound by the user. Prolonged auditory treatment using ATST, may lead to decrease in the frequency of occurrence of tinnitus. The at least one of the practitioner device and the mobile device may also administer AIT and ART, by generating acoustic waves that are of a soothing nature, in order to help the user relax and sleep.

CHaTT is a cognitive behavioral therapy that promotes the neurological process of habituation in the user. Habituation involves the gradual reduction in perception of noises associated with the auditory disorder, over time. Through habituation, the user may eventually learn to ignore the noises associated with the auditory disorder. CHaTT often involves multiple steps such as one or more of, but not limited to, educating the user about the auditory disorder, training to help the user relax, administering cognitive behavioral therapy, and exposing the user to the noises associated with the auditory disorder. For instance, educating the user involves removing misconceptions about the auditory disorder, and presenting possible treatment options for managing the auditory disorder. Training to help the user relax helps reduce negative emotional consequences of the auditory disorder. Further, providing cognitive behavioral therapy prevents the user from falling into dysfunctional cognitive patterns that intensifies the negative emotional consequences of the auditory disorder, and helps the user adopt a realistic attitude for dealing with the auditory disorder. Additionally, exposing the user to the noises associated with the auditory disorder for a prolonged period may help the user habituate to the noises associated with the auditory disorder.

AIT, and ART, involve using a combination of sound therapy and psychological counselling for providing relief to the user. By generating acoustic waves of a soothing nature, the negative emotional consequences of the auditory disorder may be reduced. For example, generating acoustic waves of a soothing nature may help the user reduce anxiety and overcome insomnia.

Figure 2:
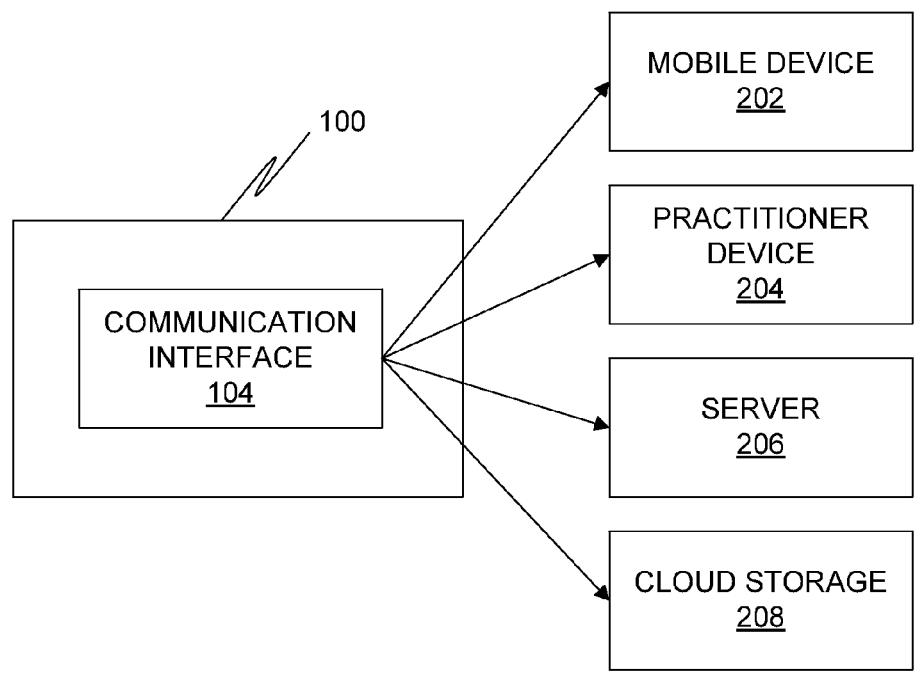
FIG. 2 illustrates communication of information between the practitioner device and one or more remote devices such as, but not limited to, a mobile device, a cloud storage, and a server, using the communication interface of the mobile device, in accordance with an embodiment.

Components of the practitioner device 100 that may be used to facilitate one or more of, the auditory test and the auditory treatment procedure are illustrated in FIG. 1. The components may be one or more of, but not limited to, a user interface 102 and a communication interface 104. The practitioner device 100 is explained in further detail in conjunction with FIG. 3 below. The user interface 102 configured for receiving an input from a practitioner. Based on the input provided by the practitioner, the communication interface 104 is configured to communicate information between the practitioner device 100 and at least one of a mobile device 202 and another practitioner device 204 over at least one of a wired communication channel and a wireless communication channel as illustrated in FIG. 2.

In an embodiment, the practitioner device 100 may communicate with one or both of a server 206 and a cloud storage 208. Additionally, the practitioner using the practitioner device 100 may download the information into an expert database in the cloud storage 208. Other information belonging to the practitioner such as, but not limited to, data, records, scientific articles and user reports, may also be stored in the expert database. Moreover, the cloud storage 208 may also store a popular science database for containing scientific articles relevant to the user and the practitioner.

In another embodiment, the mobile device 202 may store data in the cloud storage 208. The practitioner using the practitioner device 100 may then access the cloud storage 208 to obtain data corresponding to the user of the mobile device 202. In an instance of the embodiment, the cloud storage 208 may be used to store information pertaining to the user. Additionally, a user account may be registered in the cloud storage 208 for the user. The user account may be used for containing all information pertaining to the user. Further, cloud storage 208 may store information pertaining to the practitioner operating the practitioner device 100, and at least one other practitioner operating another practitioner unit. Using the cloud storage 208, the practitioner operating the practitioner device 100 may then access information pertaining to another practitioner operating another remote unit, and vice versa.

Figure 3:
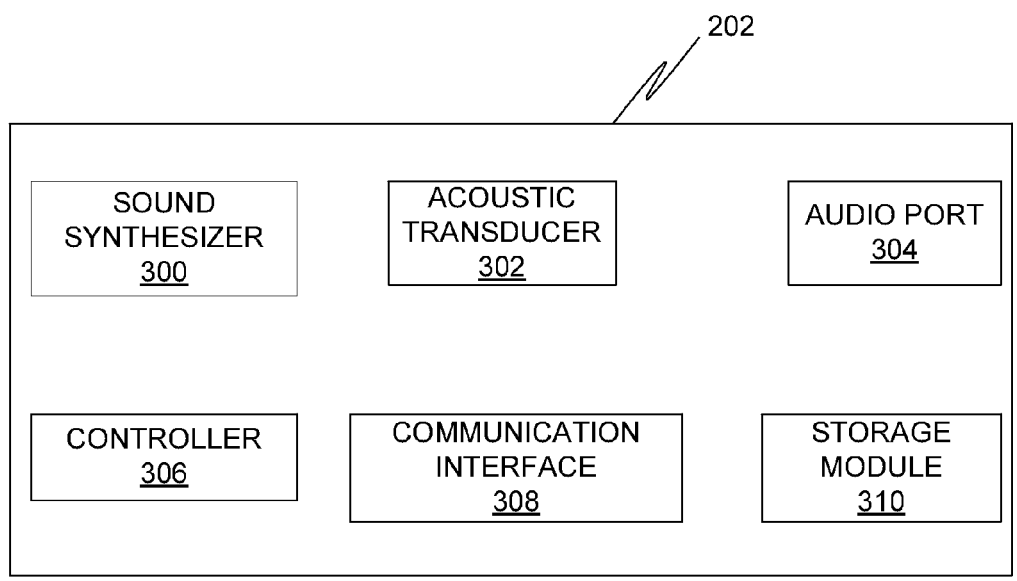
FIG. 3 illustrates a mobile device for facilitating one or more of testing and treatment of an auditory disorder, in accordance with an embodiment.

The information communicated by the practitioner device 100 to the mobile device 202 via the communication interface 104 corresponds to at least one of at least one auditory test and at least one auditory treatment procedure. In an embodiment, the information includes at least one parameter, wherein the sound synthesizer is configured for generating the at least one sound signal in accordance with the at least one parameter, wherein the at least one parameter is based on at least one of the at least one auditory test and the at least one auditory treatment procedure. Thereafter, the mobile device facilitates at least one of testing of at least one auditory disorder and treatment of at least one auditory disorder. Components of the mobile device 202 that may be used to perform one or more of, the auditory test and the auditory treatment procedure are illustrated in FIG. 3. The components may be one or more of, but not limited to, a sound synthesizer 300, an acoustic transducer 302, an audio port 304, a controller 306, a communication interface 308 and a storage module 310. In an embodiment, at least one of the sound synthesizer 300, the acoustic transducer 302, the audio port 304, the controller 306, and the storage module 310 are included in the practitioner device 100.

The sound synthesizer 300 is configured for generating the sound signal needed in performing one or more of, the auditory test and the auditory treatment procedure. Further, the sound signal may be generated based on a parameter corresponding to the sound signal. The parameter may be one or more of, but not limited to, a pitch, a tone, a loudness, a volume, an amplitude, a phase, a phase shift, an intensity, a frequency, a bandwidth, a noise, a speech, a rhythm, a start time, an end time and a periodicity. In an embodiment, the parameter used in performing the auditory test may be different from another parameter used in performing the auditory treatment procedure.

Further, the sound synthesizer 300 may comprise a module such as one or more of, but not limited to, a compatible digital signal processor (DSP), a sound card, a central processing unit (CPU), a software module and a speaker, for facilitating the generation of the sound signal. Further, the module of the sound synthesizer 300 may enable generating the sound signal in accordance with standards for sound synthesis such as, but not limited to, Musical Instrument Digital Interface (MIDI).

Additionally, the sound synthesizer 300 may perform screening and calibration of parameters. For instance, the sound synthesizer 300 may allow screening and calibration of frequency and loudness, of the sound signal. Moreover, adjustment of loudness may be carried out using mechanisms such as one or more of, but not limited to, static manual adjust, dynamic increment steps, dynamic varying speed, discontinuous experimental signal calibration with one or more sound levels and continuous experimental signal calibration with one or more sound levels. Further, the sound synthesizer 300 may allow for both manual and automatic, screening and calibration.

In an embodiment, the sound synthesizer 300 may allow automatic adjustment of the parameter of the sound signal, for performing one or more of, the auditory test and the auditory treatment procedure. In another embodiment, the sound synthesizer 300 may allow for manual adjustment of the parameter of the sound signal to be generated. Additionally, the adjustment of the parameter of the sound signal to be used in the auditory test may differ from an adjustment of the parameter of another sound signal to be used in the auditory treatment procedure. In another embodiment, a user operating the mobile device 202 may be allowed to modify the parameter of the sound signal using the user interface of the mobile device 202.

Further, the sound synthesizer 300 may use an algorithm such as one or more of, but not limited to, a logical algorithm and an analytical algorithm, for synthesizing the sound signal. The algorithms may utilize signal-processing techniques such as one or more of, but not limited to, nonlinear, non-stable, dynamic and additive signal processing. Moreover, parameter variables of the algorithm may be, one or more of, but not limited to, sound signal waveform, time, amplitude and phase angle. Additionally, the algorithm may be implemented by one or more software modules in the sound synthesizer 300 for generating the sound signal. In an instance, the sound synthesizer 300 may use an analytical algorithm for generating the sound signal. Additionally, the sound synthesizer 300 may use one or more of a time domain signal and a frequency domain signal, in conjunction with the analytical algorithm for generating the sound signal.

Further, the mobile device 202 may also include the acoustic transducer 302 for generating acoustic waves based on the sound signal received from the sound synthesizer. Further, the acoustic transducer 302 may allow for generation of acoustic waves in a range of a parameter needed for testing and treating the auditory disorder. Additionally, in an embodiment, the range of the parameter to be used in the auditory test may differ from the range of the parameter to be used in the auditory treatment procedure. In an embodiment, the frequency of the acoustic waves generated may be, but not limited to, the range of 1 Hz to 20 KHz. In addition, the intensity of the acoustic waves generated may be, but not limited to, the range of 0 dB to 120 dB. In an instance, the acoustic transducer 302 may be earphones, capable of generating the acoustic waves characterized by the range of the parameter needed for testing and treating the auditory disorder.

The mobile device 202 may also include the audio port 304 for functioning as an interface to the acoustic transducer 302. For example, the audio port 304 may be used as an interface for plugging in the earphones.

Additionally, the mobile device 202 may include the communication interface 308 for exchanging information between the mobile device 202 and the practitioner device 100 as illustrated in FIG. 2. The mobile device 202 may also communication with the cloud storage 208 and the server 206. One or more communication channels such as, but not limited to, a wireless and a wired channel, may be used for exchanging information between the mobile device 202 and at least one of the practitioner device 100, the cloud storage 208 and the server 206. The wireless channel may be, but not limited to, Bluetooth, wireless internet, infrared, near field communication and radio frequency. Moreover, the communication interface 308 may exchange information pertaining to one or more of, the auditory test and the auditory treatment procedure. Additionally, in an embodiment, the information pertaining to the auditory test may be different from the information pertaining to the auditory treatment procedure.

Further, the communication interface 308 may be configured for receiving information from the practitioner device 100. The information received may include, but is not limited to, the sound signal, the parameter corresponding to the sound signal, the result of the auditory test, the auditory test, the auditory treatment procedure and a counselling protocol from the remote location. Further, the parameter may be based on the auditory test and the auditory treatment procedure. Additionally, the communication interface 308 may be capable of receiving information stored in the storage module 310 of the mobile device 202.

The communication interface 308 may also be configured for transmitting information. The information transmitted may include, but not limited to, the sound signal, a parameter corresponding to the sound signal, the auditory test, a result of the auditory test, the auditory treatment procedure and a counselling protocol. Further, the parameter of the sound signal may be based on at least one of, the auditory test and the auditory treatment procedure. Additionally, the communication interface 308 may be capable of transmitting information stored in the storage module 310 of the mobile device 202.

Further, the storage module 310 of the mobile device 202 may be configured for storing information related to the auditory treatment procedure and the auditory test. Additionally, the information related to the auditory test may be different from, the information related to the auditory treatment procedure. The information may include one or more of, but not limited to, the sound signal, a parameter corresponding to the sound signal, a result of the auditory test, a result of the auditory treatment procedure, information corresponding to psychological training and counselling, the result of assessing the auditory test, a library of sound signals to be used in treating the auditory disorder, protocols for conducting the auditory test, a treatment therapy expert database and a training material database. For example, the library of sound signals may comprise a tinnitus sound database for storing sound signals to be administered in treating tinnitus.

The controller 306 may be configured for controlling at least one of, the sound synthesizer, the acoustic transducer 302 and the audio port 304, in order to facilitate testing and treatment of the auditory disorder. Further, the controller 306 may comprise one or more of electronic circuitry and software algorithms, configured for at least one of nonlinear, non-stable and additive signal processing, for enabling diagnosis and treatment of the auditory disorders. The software algorithms may include one or more of, but not limited to, analytical algorithms and logical algorithms.

Additionally, the controller 306 may be a processing unit such as one or more of, but not limited to, a microprocessor, a microcontroller 306, a CPU and a DSP. Further, in an embodiment, the controller 306 may receive a set of instructions for facilitating the administering of the auditory test and the auditory treatment procedure. Additionally, the set of instructions to be used in facilitating the auditory test may be different from, the set of instructions used in facilitating the auditory treatment procedure.

Based on the set of instructions received, the controller 306 may modify the parameter corresponding to the sound signal to be generated for performing the auditory test and the auditory treatment procedure. Thereafter, the controller 306 may control one or more of, the sound synthesizer, the acoustic transducer 302 and the audio port 304 for generating the acoustic waves based on the modified parameters.

Alternatively, in another embodiment, based on analyzing information the controller 306 may automatically issue a set of instructions for performing one or more of, the auditory test and the auditory treatment procedure. For example, the controller 306 may analyze information pertaining to the result of the auditory test. Based on the result, the controller 306 may automatically select the auditory treatment procedure to be administered. Thereafter, the controller 306 may issue the set of instructions, for controlling one or more of the sound synthesizer, the acoustic transducer 302 and the audio port 304, for generating a sound signal to be used in administering the auditory treatment procedure.

In an embodiment, the controller 306 may control the sound synthesizer 300 for the left ear, hereinafter referred to as the left ear sound synthesizer, and another sound synthesizer 300 for the right ear, hereinafter referred to as the right ear sound synthesizer. In an instance, the controller 306 may copy the sound signal generated by the left ear sound synthesizer onto the right ear sound synthesizer, and vice versa. Subsequently, adjustments may be made to customize the sound signal in accordance with the requirements of each ear.

In another embodiment, the controller 306 may be configured for performing testing and treatment in one or more modes such as, but not limited to, a synchronous mode and an asynchronous mode, of delivering acoustic waves to both left and right ears.

In the synchronous mode of adjustment, the sound signal to be generated for the right ear, and the sound signal to be generated for the left ear, may be modified by the controller 306 in a manner that is dependent. Whereas, in the asynchronous mode of adjustment, the controller 306 may independently modify the sound signal to be delivered to the left ear, and the sound signal to be delivered to the right ear. Moreover, in the synchronous mode of operation, the modification for both ears may occur simultaneously. For example, the controller 306 may deliver an auditory test for tinnitus to the left ear, and another auditory test for hearing loss to the right ear, simultaneously. In an embodiment, selection of the mode of operation may occur automatically. In an alternative embodiment, a user operating the mobile device 202 may specify the mode of operation by interacting with the user interface of the mobile device 202.

Further, the controller 306 may be configured for controlling the sound synthesizer 300 based on the result of the auditory test and the result of the auditory treatment procedure. Additionally, the result may be, but is not limited to, the sound signal, the parameter corresponding to the sound signal, the auditory test, the result of the one auditory test, the result of the auditory treatment procedure, the counselling protocol, a centre frequency of hearing loss, a tinnitus masking frequency range and a pure tone audiogram. Further, the result may be expressed in any form such as, but not limited to, text, figure, graphic, audio and video format.

Additionally, the controller 306 of the mobile device 202 may also control the storage module 310 of the mobile device 202. Operating the storage module 310 may involve, storing, recording, managing and processing, information related to patient information, the auditory test and the auditory treatment procedure. For example, the library of sound signals in the storage module 310 may be used by the controller 306 for convenient use, storage, classification and selection of the sound signal to be used in treating the auditory disorder.

Moreover, the controller 306 may also organize individual records for each user using the mobile device 202 in the storage module 310. Further, records may also be organized and sorted in a hierarchical manner. Additionally the levels of the hierarchy may be, but are not limited to, the type of auditory disorder, the severity of auditory disorder and the type of auditory treatment procedure. For example, records may be categorized based on a severity of tinnitus. In an instance, the controller 306 may prevent alteration to the records. In another instance, the controller 306 may restrict access to modification of the records. Control for modifying the records may be selectively given to a user such as, but not limited to, an administrator, a clinical expert and a doctor.

Further, the controller 306 may allow information stored in the storage module 310 to be exchanged with a remote location using the communication interface 308.

In an embodiment, the controller 306 may allow exchanging information contained in the storage module 310 with at least one of the practitioner device 100, the server 206 and the cloud storage 208. A practitioner operating the practitioner device 100 may modify one or more of, the auditory test and the auditory treatment procedure, to be administered based on information received from the mobile device 202. The practitioner operating the practitioner device 100 may be one or more of, but not limited to, a clinical expert and a doctor.

For example in accordance with the embodiment, the controller 306 may send the result of performing the auditory test, to the practitioner device 100. A practitioner may then analyze the result and modify the parameter of the sound signal to be used in administering the auditory treatment procedure. Thereafter, the practitioner may send the modifications using the practitioner device 100 to at least one of the mobile device 202, the server 206 and the cloud storage 208 for storage in the library of sound signals. The controller 306 may subsequently access the library of sound signals when administering the auditory treatment procedure, and generate the sound signal based on the modifications to the parameter. Thereafter, the controller 306 may operate the sound synthesizer 300 to generate the sound signal to be used for administering the auditory treatment procedure. Subsequently, user may directly interact with the practitioner, and communicate the efficacy of the auditory treatment procedure to the practitioner. The user and the practitioner may then work together to fine tune the auditory treatment procedure to be delivered to the user in future.

Further, the controller 306 may also allow the practitioner device 100 to control the operation of the mobile device 202. Remote control of the mobile device 202 may be enabled by using the communication interface 308 of the mobile device 202. Additionally, remote control of the mobile device 202 may occur on a real time basis. For example, if the user requires urgent attention from the practitioner, real time remote control of the mobile device 202 may be provided to the practitioner. Additionally, operation software and a mobile application may be used to connect the mobile device 202 through wireless internet to the practitioner.

Furthermore, the controller 306 may facilitate performing the auditory test, using the components of the mobile device 202, and at least one module interfaced with the mobile device 202. For instance, the at least one module may be a digital aural endoscope used in obtaining images of parts of the ear such as, but not limited to, the ear canal and the ear drum. The controller 306 may subsequently store the images taken by the endoscope in the storage module 310. Additionally, the controller 306 may also incorporate the images into a comprehensive digital report containing the result of conducting the auditory test. Further, at least one of the images and the comprehensive report may be stored temporarily in the storage module 310 for further analysis by the controller 306.

Subsequently, in an instance, the user may choose to output at least one of the images and the comprehensive report to a printer. Alternatively, in another instance, one or more of, the images and the comprehensive report may be transmitted by the controller 306 to at least one of the practitioner device 100, the server 206 and the cloud storage 208. The practitioner at the practitioner device 100 may then analyze the images to assess the state of the ear, and prescribe the auditory treatment procedure to be administered by the mobile device 202 to the user. The state of the ear may be, but is not limited to, ear disease, damage, inflammation, earwax embolism and narrow ear canals.

In an embodiment, the controller 306 may facilitate performing the auditory test for hearing loss. The controller 306 may perform the auditory test by generating the sound signal using the sound synthesizer, and measuring the response of the user to the sound signal. The result of testing the hearing loss may then be stored in the storage module 310. The result of the auditory test for hearing loss may include one or more of, but not limited to, a hearing loss central frequency, a relevant tinnitus masking frequency range and a pure tone audiogram. Thereafter, the user may output the result to a printer for analysis. Additionally, the result may be transferred to at least one of the practitioner device 100, the server 206 and the cloud storage 208 to be analyzed by the practitioner. Further, the result may be stored temporarily in the storage module 310 for analysis by the controller 306.

Further, in accordance with the embodiment, the type of auditory test performed may be one or more of, but not limited to, a subjective test, an objective test and a speech hearing ability test. In an instance, the auditory test conducted for measuring hearing loss may be one or more of, but not limited to, a subjective pure tone hearing test, an objective acoustic impedance admittance measurements (OAE), an auditory brainstem response (ABR), an auditory steady-state evoked response (ASSR), a real ear analysis and a speech assessment. The controller 306 may select one or more characteristics of the sound signal for conducting the auditory test. The one or more characteristics may be, but not limited to, a single tone, a pure tone, a synthesized tone, a single rhythm, a complex tone, a complex rhythm, a simulated natural sound, an animal bulking and a human speech signal. The controller 306 then operates the sound synthesizer 300 to generate the sound signal in accordance with the one or more characteristics selected. Further, the controller 306 may also adjust the parameter of the sound signal according to the type of auditory test to be administered for measuring hearing loss.

Additionally in the embodiment, the controller 306 may generate the pure tone for testing hearing loss in a normal noisy environment. Further, the amplitude of the pure tone may be within, but is not limited to, the range of 0-120 db, and the frequency of the pure tone may be within the range of, but is not limited to, 0 to 20,000 Hertz. Moreover, the controller 306 may also simulate a noisy environment surrounding the user. Further, the controller 306 may perform one or more of, noise masking, background environment analysis, real ear analysis and a surround sound field assessment, for simulating the noisy environment.

In an embodiment, the controller 306 may capture and playback acoustic waves for testing and treating the auditory disorder. Further, the controller 306 may generate the sound signal using the sound synthesizer. The sound signal generated may be in the range of 0-100 db, and 1-20,000 Hz.

Further, the controller 306 may cause the sound signal to be generated in one or more stages. For example, at a first stage of generation, a first sound synthesizer and a second sound synthesizer may be used for generating a first sound signal and a second sound signal, over multiple channels. Subsequently, the first sound signal and the second sound signal may be combined to form a synthesized sound signal. The parameter of the synthesized sound signal may be varied by changing the contribution of each channel in generating the synthesized sound signal. For example, changing the contribution by each channel may involve, changing a given level of the parameter corresponding to the sound signal.

Additionally, the type of sound signal produced may be one or more of, but not limited to, a pure tone, a noise, a pulse and a recorded sound. Similarly, the tone of the sound signal produced may be one or more of, but not limited to, regular pure sound, synthesis pure sound, pulse pure sound and mix-pulse sound. The noise associated with the sound signal includes one or more of, but not limited to a white noise, a colored noise and a filter-transferred noise. Further, characteristics of the noise such as one or more of, but not limited to, a frequency, a range, a tone, a rhythm and a loudness, may be adjusted in order to customize testing and treatment of the auditory disorder. Additionally, the loudness of each sound signal generated may be adjusted using a switch.

Further, the second stage of generation may involve adding a pre-shaped sound signal to the synthesized sound signal received from the first level. The waveform of the pre-shaped sound signal may include one or more of, but not limited to, a straight line, an impact, a slope, a zigzag, a trigonometric function, a trapezoid, a rectangular and a pulse, waveform. Further, the waveform added may be made adjustable in order to customize testing and treatment of the auditory disorder.

Additionally, at the third stage of generation, background sounds may be added to the sound signal received from the second stage. The background sounds may be one or more of, but not limited to, background music, nature sounds and other synthesized sounds.

According to the embodiment, in an instance the controller 306 may perform capture and playback of acoustic waves for treating tinnitus. Capture and playback of acoustic waves may involve, matching and capturing the sound signal capable of providing the best relief for treating the target tinnitus sound, specific to the user. Additionally, the controller 306 may allow customizations to be made to the sound signal for providing the target tinnitus sound. The customization may be based on factors such as, but not limited to, a side of the ear, a time of the day and a current environment of the mobile device 202. Other adjustments such as selecting the synchronous and the asynchronous, mode of delivering the sound signal to both the left ear and the right ear, may also be allowed. Moreover, the parameter of the sound signal may be varied to identify the sound signal that best masks the target tinnitus sound.

Further, in the instance, the controller 306 may automatically generate the sound signal to be used for matching and capturing the target tinnitus sound, using information in the storage module 310. The controller 306 may additionally use information such as, data stored in the tinnitus sound database for automatically generating the sound signal. Alternatively, in accordance with the instance, the controller 306 may obtain a reference sound signal from the remote location, and subsequently modify the reference signal to match and capture the target tinnitus sound.

Furthermore, in accordance with the instance, subsequent to generating the sound signal for treating tinnitus, the controller 306 may allow the user to adjust the parameter of the sound signal. Adjusting the parameter may enable the user to find a setting of the parameter that provides the best match to the target tinnitus sound. The user may interact with the user interface of the mobile device 202 for adjusting the parameter. Alternatively, control over modifying the sound signal may be limited to the practitioner at the practitioner device 100. In yet another alternative, the controller 306 may automatically modify the sound signal without any user input. Further, the controller 306 may take into account subjective information such as, but not limited to, information provided by the user during psychological training and counselling, in selecting and modifying the sound signal to be delivered.

In an embodiment, the controller 306 may facilitate testing and treatment of the auditory disorder by providing psychological training and counselling. Providing psychological training and counselling may include one or more of, but not limited to, performing psychological assessment, providing behavior cognition therapy, psychological guidance planning and psychological training.

Further, in accordance with the embodiment, the controller 306 may provide psychological assessment by having a user provide information pertaining to the psychological ramifications of the auditory disorder affecting the user. The user may provide information such as one or more of, but not limited to, a perceived level of the auditory disorder, efficacy of the auditory treatment procedure received so far, and factors contributing to exacerbating the auditory disorder.

In an instance of the embodiment, the controller 306 may provide a self-assessment questionnaire to the user. The information received from the user may comprise, the answers provided by the user in the self-assessment questionnaire. Further, the information provided in the self-assessment questionnaire may be formulated in a question and answer psychological table, scored against standardized answers, and then subsequently summarized into a report by the controller 306. Subsequently, the report may be transmitted by the controller 306 using the communication interface 308 to at least one of the practitioner device 100, the server 206 and the cloud storage 208. The practitioner operating the practitioner device 100 may then assess the report, and provide feedback to the user as a part of providing the auditory treatment procedure. Feedback may be transmitted to the mobile device 202 from the practitioner device 100 for easy access by the user. The feedback may be, but is not limited to, the counselling protocol, and a customized plan and execution procedure, to be implemented by the user.

In another instance of the embodiment, the controller 306 may facilitate performing auditory treatment procedure by providing behavior cognition therapy. By providing behavior cognition therapy one or more of, a mood of the user and cognition, may be improved. The controller 306 may provide information to reform thinking, belief and action of the user, as means of providing the behavior cognition therapy. Further, the controller 306 may modify the behavior cognition therapy to be provided, based on information provided by the user. By providing the behavior cognition therapy the controller 306 may enable a user to handle the auditory disorder by training the user to slowly ignore the noises associated with the auditory disorder over time.

Further, in accordance with the embodiment, the controller 306 may provide psychological training by providing training files using formats such as, one or more of, but not limited to video, audio and text. The training files may include information such as, one or more of, but not limited to the counselling protocol, and the customized counselling plan and execution procedure. Moreover, the training files may enable the user to self-manage auditory disorders.

In an instance of the embodiment, the user may receive the training files from the remote location, thereby enabling psychological training in situations when the user is away from a hospital. Additionally, the user may also fill a report subsequent to performing one or more steps in the training files, and transmit the report to at least one of with the practitioner device 100, the cloud storage 208 and the server 206. The practitioner operating the practitioner device 100 may read the report and further customize the training materials to be sent to the user.

In an embodiment, subsequent to performing the auditory test, the controller may send the result of the auditory test to the remote location for assessment. Alternatively, in another embodiment, subsequent to performing the auditory test, the controller 306 may automatically assess the result of performing the auditory test. The controller 306 may be capable of assessing separately the results of each auditory test conducted by the mobile device 202. The controller 306 may also be capable of combining and analyzing the result of a first auditory test with a second auditory test, together. Additionally, other information such as one or more of, but not limited to, images taken by the digital endoscope, information obtained from the user during psychological counselling and training, and information stored at the remote location, may also be taken into account during assessment. For example, the controller 306 may be able to combine and analyze together, the result of conducting the auditory test for hearing loss, the result of conducting the auditory test for tinnitus, images obtained from the digital endoscope and information obtained through performing psychological assessment and training.

Additionally in the embodiment, the controller 306 may perform both qualitative and quantitative assessment of the result obtained from performing the auditory test. For instance, the controller 306 may be able to classify a severity level of the tinnitus, based on the result obtained from conducting the auditory test for hearing loss and the result obtained from conducting the auditory test for tinnitus, along with information obtained from psychological training and counselling. The type of information used in assessing the severity may be one or more of, but not limited to, tone and loudness assessment results, counselling results and, self-assessment questionnaire analysis scores. Further, the controller 306 may provide a comprehensive report of the result obtained from assessing the auditory test, with at least one other auditory test.

In accordance with the embodiment, subsequent to performing the assessment, the controller 306 may store the result of the assessment in the storage module 310. Additionally, the result of the assessment may be output to a device such as, but not limited to, a printer and a touch screen.

In an embodiment, the controller 306 may receive instructions from the remote location for performing the auditory treatment procedure.

Alternatively, in another embodiment, the result of the assessment may be used by the controller 306 for automatically facilitating the auditory treatment procedure. Facilitating the auditory treatment procedure may involve one or more of, but not limited to, selecting, requesting, creating and modifying, the auditory treatment procedure to be provided to the user. Further, the controller 306 may also be able to use the result of assessing one auditory disorder and at least one other auditory disorder, in facilitating the auditory treatment procedure. Further, the controller 306 may use the result of assessment in simultaneously administering the auditory treatment procedure for one auditory disorder and at least one other auditory disorder. For example, the controller 306 may analyze the result of assessment from conducting the auditory test for hearing loss, and the auditory test for tinnitus. The analysis may reveal that by decreasing the threshold at a given frequency, the target tinnitus sound may be reduced and hearing at other frequencies may be improved. The controller 306 may then accordingly facilitate the auditory treatment procedure by decreasing the threshold at the given frequency.

Further, in accordance with the embodiment, the controller 306 may also perform assessment of the result obtained after administering the auditory treatment procedure, for analyzing the efficacy of the auditory treatment procedure already administered.

In an embodiment, the controller 306 may administer the auditory treatment procedure of sound therapy. The controller 306 may perform sound therapy by generating acoustic waves providing a therapeutic effect to a user operating the mobile device 202. Different types of sound therapies such as one or more of, but not limited to, physical interference, sound sensitivity treatment, ATMT, ATRT and ATST may be provided. In an instance, the controller 306 may obtain the sound signal from the remote location. Additionally, the controller 306 may save the sound signal in the storage module 310, and subsequently access the sound signal for generating the acoustic waves using the acoustic transducer 302 and the audio port 304.

In an embodiment, the practitioner device 100 includes at least one sensor configured to sense at least one of sound perception for performing a Subjective Pure Tone Hearing Test, bone conduction for performing a Bone Conductive Hearing Test, Objective Acoustic Impedance, Auditory Brainstem Response and Auditory Steady-State Evoked Response. In an instance of the embodiment, at least one of the practitioner device 100 and the mobile device 202 includes at least one sensor configured for performing at least one of real-ear measurement and surround sound field assessment.

Figure 4:
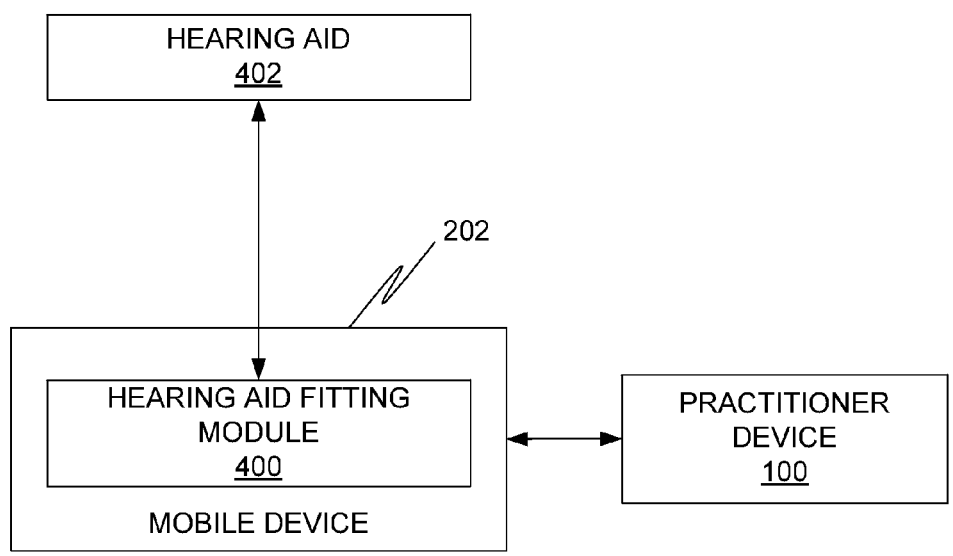
FIG. 4 illustrates configuration of a hearing aid by using a hearing aid fitting module included in the mobile device, in accordance with an embodiment.

In an instance of the embodiment, the controller 306 may facilitate the auditory treatment procedure by controlling a hearing aid fitting module 400 as shown in FIG. 4. The hearing aid fitting module 400 may be used for providing a configuration input to a hearing aid 402, interfacing with the mobile device 202. The configuration input provided by the controller 306 to the hearing aid fitting module 400 may include, but is not limited to one or more of, the sound signal, a parameter for the sound signal and a type of the sound signal.

Additionally in the instance, the hearing aid fitting module may be used by the controller 306 in administering the auditory treatment procedure for the user suffering from hearing loss. The hearing aid fitting module 400 may also be used by the controller 306 in configuring the hearing aid 402 in one or more of, the synchronous mode and the asynchronous mode, of administering treatment to the left and right ear.

In accordance with the instance, the controller 306 may automatically analyze the result of assessment and facilitate the auditory treatment procedure by fitting the hearing aid 402 to improve the hearing of a user suffering from hearing loss. Alternatively, a practitioner at the practitioner device 100 may be able to fit the hearing aid 402 based on information transmitted by the controller 306 to the practitioner device 100. The information may be one or more of, but not limited to, the result of the auditory test, the result of assessing the auditory test, images taken by the digital endoscope, and information obtained through psychological training and counselling.

In another instance, in accordance with the embodiment, the controller 306 may also facilitate the auditory treatment procedure for the auditory disorder of tinnitus. The controller 306 may facilitate auditory treatment procedure by facilitating one or more of, but not limited to, physical acoustic interference treatment, physiological counselling, and tinnitus sound matching and capturing.

Further, in the instance, the controller 306 may analyze information from one or more sources for facilitating the auditory treatment procedure for tinnitus. The one or more sources may include, but is not limited to, the storage module 310 and the remote location. Additionally, the information may include the result of assessment for the auditory test, and the result of the auditory test, for tinnitus. The information may also include, but is not limited to, images from the digital endoscope, information obtained from the user through psychological counselling and training, and information obtained from the remote location. Further, the information obtained from the remote location may include one or more of, but not limited to, input from the practitioner, and information stored in the cloud storage 208.

Thereafter in accordance with the instance, the controller 306 may apply built-in treatment formula based on the results of analyzing the information, for generating the sound signal to be used in treating tinnitus. The sound signal may be generated for both synchronous and asynchronous, mode of the auditory treatment procedure for both the left and right ears. Additionally, the controller 306 may only be configured to deliver only one of, the active auditory treatment procedure and the passive auditory treatment procedure. Alternatively, the controller 306 may be able to combine and simultaneously deliver the passive auditory treatment procedure and the active auditory treatment procedure. Subsequent to administering the auditory treatment procedure for tinnitus, the controller 306 may perform actions such as one or more of, but not limited to storing, printing, displaying and transmitting, to the remote location, the result of the auditory treatment procedure.

Alternatively, in accordance with the method and systems disclosed herein, the mobile device 202 of the present invention may also be configured as a plug-in device to be interfaced with a base unit, for facilitating the testing and treatment of the auditory disorder. The plug-in device may be interfaced with the base unit using one or more of a wired and a wireless connection. The base unit may be part of one or more of a computer, a laptop, a tablet computer and a smart phone.

The plug-in device may be one or more of, but not limited to earphones, the hearing aid 402, a special purpose tinnitus treatment device and an mp3 player. Moreover, the plug-in device may communicate with components of the mobile device 202 through a channel such as one or more of, but not limited to, a wireless channel and a wired channel. Further, the plug-in device may be a self-contained device comprising components such as, computer memory, sound card, batteries, wired communication interfaces, wireless communication interfaces and earphones.

In one embodiment, the plug-in device may comprise components such as, but not limited to, one or more of, the sound synthesizer 300, the acoustic transducer 302, the audio port 304, the controller 306, the communication interface 308 and the storage module 310, described in FIG. 1.

Additionally, the communication interface 308 may be configured for enabling communication of information between the plug-in device and the base unit. Further one or more of, the plug-in device and the base unit, may be configured for communicating with the remote location.

Additionally, communication with the remote location may occur over one or more communication channels such as, but not limited to a wired and a wireless communication channel. In one embodiment, communication with the practitioner device 100 occurs over the wireless communication channel.

In an embodiment, the plug-in device may be a special purpose tinnitus treatment device that interfaces with the base unit through one or more of, a wired and a wireless channel. Further, the special purpose tinnitus treatment device may be a self-contained device comprising components such as, but not limited to, computer memory, sound card, batteries, wired communication interface, wireless communication interface and earphones. Additionally, the special purpose tinnitus treatment device may communicate with the practitioner device 100, through the base unit.

Figure 5:
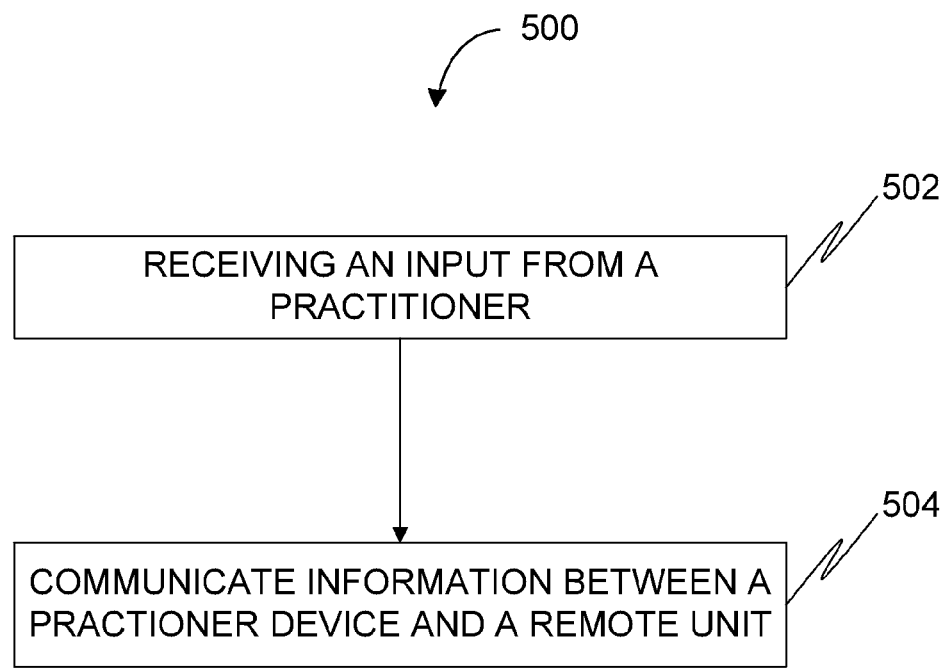
FIG. 5 illustrates a flow chart of a method for one or more of testing and treatment of an auditory disorder, in accordance with an embodiment.

According to methods and systems disclosed herein, the mobile device 202 may facilitate testing and treatment by performing the following steps of a method 500, as illustrated in FIG. 5.

In step 502, the method may involve receiving an input from a practitioner via the practitioner device 100. The input is related to at least one of testing and treatment of at least one auditory disorder. Based on the input, in step 504, information is exchanged between the practitioner device 100 and a remote unit including the mobile device 202 of a user, the server 206 and the cloud storage 208.

Figure 6:
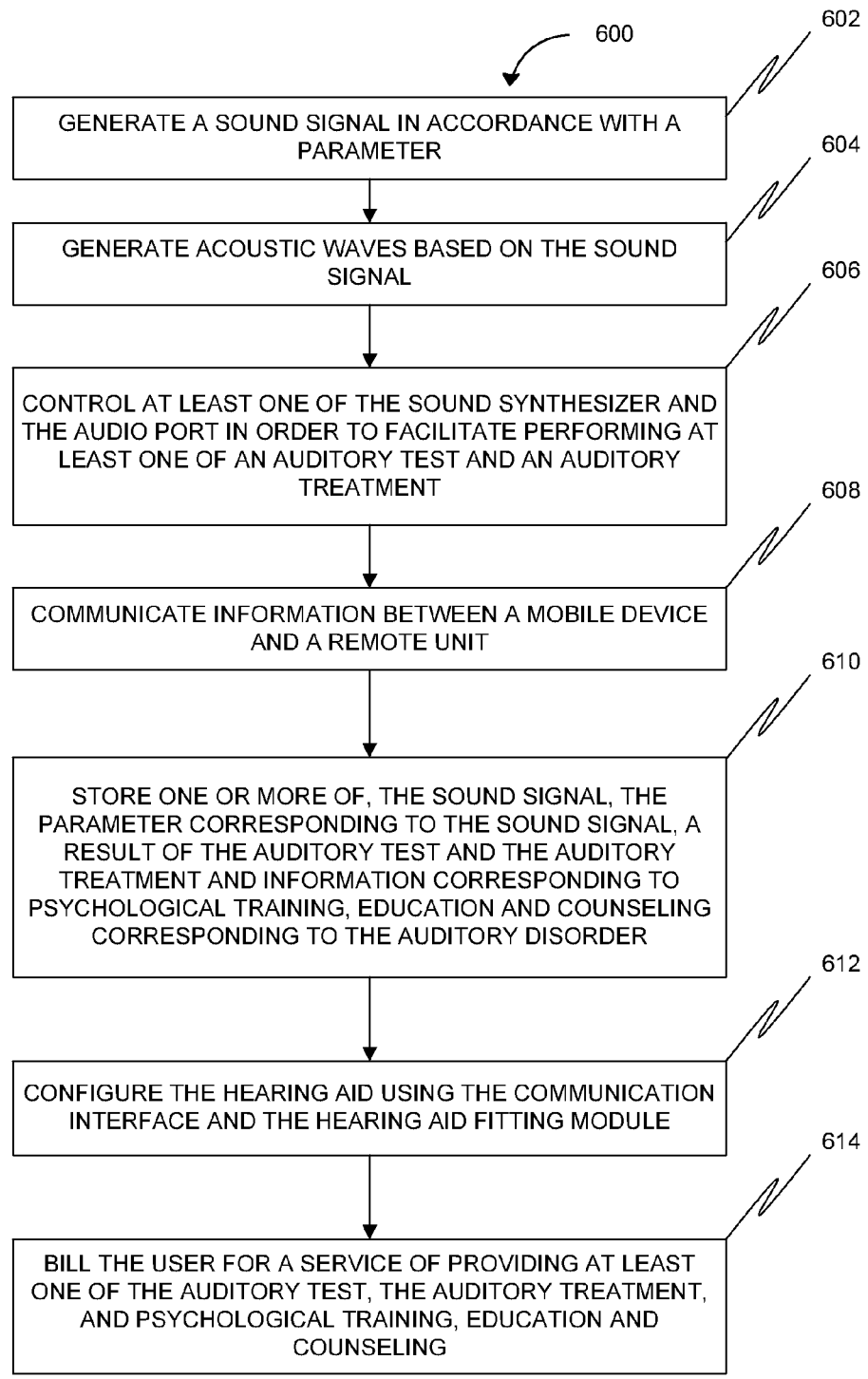
FIG. 6 illustrates a flow chart of a detailed method for one or more of testing and treatment of an auditory disorder, in accordance with an embodiment.

Thereafter, the mobile device 202 facilitates at least one of testing of at least one auditory disorder and treatment of at least one auditory disorder. The next steps are explained in detail in conjunction with the steps of a method 600 illustrated in FIG. 6. At 602, the method may involve generating the sound signal using the sound synthesizer 300. Additionally, generation of the sound signal may also depend on information received from sources such as, one or more of, a user interface of the mobile device 202, the storage module 310, the practitioner device 100, the server 206 and the cloud storage 208.

For instance, a practitioner operating the practitioner device 100 may specify the parameter of the sound signal to be generated by the sound synthesizer, as mentioned in embodiments described above. In another instance, the user operating the mobile device 202 may specify the sound signal to be generated by interacting with the user interface of the mobile device 202. In yet another instance, the sound signal may be downloaded from the cloud storage 208 to the library of sound signals, and subsequently selected by the user for generation by the sound synthesizer.

Thereafter, acoustic waves based on the sound signal may be generated using one or more of, the acoustic transducer 302 and the audio port 304, in step 604.

Subsequently in step 606, the method may involve using the controller 306 for performing one or more of, the auditory test and the auditory treatment procedure. The controller 306 may be used for controlling at least one of, the sound synthesizer 300 and the audio port 304, for performing the auditory test and the auditory treatment procedure. In an instance, the controller 306 may administer a first auditory test for a first auditory disorder, and a second auditory test for a second auditory disorder, simultaneously to the user operating the mobile device 202. Similarly, the controller 306 may also administer a first auditory treatment procedure for a first auditory disorder and a second auditory test for a second auditory disorder, simultaneously to the user operating the mobile device 202. Further, the first auditory treatment procedure may be the passive auditory treatment procedure, while the second auditory treatment procedure may be the active auditory treatment procedure. In an instance, the controller 306 may also provide one or more of, the synchronous and the asynchronous mode, of administering one or more of, the auditory test and the auditory treatment procedure, to both the left and right ears of the user. Additionally, the controller 306 may also enable receiving input from the user from the user interface for adjusting the parameter of the sound signal to be administered as a part of the auditory test and the auditory treatment procedure.

The method may also involve a step 608 of communicating information between the mobile device 202 and the remote location. Communication of information may include transmission of information. For instance, this step may involve communicating information such as, self-assessment questionnaire forms, the result of assessment of the auditory test, and the result of the auditory test. Information may be transmitted to the remote location. Practitioners with access to the remote location may then access the information, and specify adjustments to the auditory test administered at the mobile device 202. The practitioners may also specify the auditory treatment procedure to be administered. In another example, the user may send messages seeking expert assistance to the cloud storage 208 through the user account registered to the user. A management system corresponding to the cloud storage 208 may then notify a practitioner connected to the cloud storage 208 with the details of the user and the nature of assistance required.

Additionally, communication of information may also include receiving information from the remote location. For instance, the step 608 may also involve receiving training material for psychological training and counselling, stored in the cloud storage 208. The user may read the training material, and fill self-assessment questionnaire forms to be subsequently transmitted to the practitioner operating the practitioner device 100. In another instance, the user may receive information such as, the sound signal for subsequently conducting the auditory test, feedback on the self-assessment questionnaire forms, and adjustments to be made to the auditory test and the auditory treatment procedure.

The method may also include a step 610 of storing information in the storage module 310.

In an embodiment, the method may further include an optional step 612, of providing the configuration input to the hearing aid 402 interfacing with the mobile device 202 using the hearing aid fitting module 400. The step 612 may occur after the step 408 of receiving information from the practitioner device 100. Alternatively, the step 612 may be performed subsequent to the step 606 of using the controller 306 to facilitate the auditory test.

Additionally, in another embodiment the method may also include an optional step 614, of billing the user for a service of providing one or more of, the auditory test and the auditory treatment procedure. Further, the billing may be based on the service provided to the user. In an embodiment, service records for each user may be stored in the cloud storage 208. The service records may contain information pertaining to all services provided to the user. Moreover, the services provided may include, but not limited to, diagnosis, assessment, treatment, psychological training and counselling, provided to the user. Based on the service records, the user may be billed for the services provided. In an instance, the cloud storage 208 may utilize a prepaid consumer purchase model for allowing the user to pre-pay for the service by using one or more of, prepaid cards and advance money deposits, to a saving account linked with the user account. Thereafter, the cloud storage 208 records information provided by the controller 306 in the mobile device 202 in the service records. Thereafter, payment may be subtracted based on the information stored in the service records. Additionally, the step 614 may occur after the step 608 of receiving information. Alternatively, the step 614 may be performed subsequent to the step 606 of using the controller 306 to facilitate the auditory test and the auditory treatment procedure. In another instance, the step 614 may be performed after step 610 of storing information in the storage module 310.

It will be appreciated that various above-disclosed embodiments, other features and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

We claim:

1. A practitioner device for facilitating at least one of testing and treatment of at least one auditory disorder, the practitioner device comprising:
a user interface configured for receiving an input from a practitioner;
a communication interface configured for communicating information between the practitioner device and at least one of a mobile device and another practitioner device over at least one of a wired communication channel and a wireless communication channel, wherein the information is based on the input, wherein the information corresponds to at least one of at least one auditory test and at least one auditory treatment procedure, wherein the mobile device facilitates at least one of testing of at least one auditory disorder and treatment of at least one auditory disorder;
a sound synthesizer configured for generating at least one sound signal, wherein the generating is in accordance with at least one parameter representing at least one of intensity, loudness, frequency, tone, bandwidth, noise, speech, rhythm, a start time, an end time and periodicity corresponding to the at least one sound signal;
an audio port configured for interfacing with an acoustic transducer configured for generating acoustic waves based on the at least one sound signal, wherein a frequency of the acoustic waves is between 1 Hz and 20 KHz, wherein an intensity of the acoustic waves is between 0 dB and 120 dB;
a controller configured for controlling at least one of the sound synthesizer and the audio port based on the information communicated by another practitioner device, wherein the controller is configured for performing at least one of the at least one auditory test and the at least one auditory treatment procedure in one of a synchronized mode and a desynchronized mode; and
a storage module configured for storing at least one of the at least one sound signal, at least one parameter corresponding to the at least one sound signal, a result of the at least one auditory test and at least one auditory treatment and information corresponding to at least one of psychological training, education and counselling corresponding to the at least one auditory disorder, wherein the at least one parameter is based on at least one of the at least one auditory test and the at least one auditory treatment procedure.

2. The practitioner device of claim 1, wherein the mobile device comprises:
the controller configured for controlling at least one of the sound synthesizer and the audio port based on the information communicated by the practitioner device.

3. The practitioner device of claim 2, wherein the information comprises at least one parameter, wherein the sound synthesizer is configured for generating the at least one sound signal in accordance with the at least one parameter, wherein the at least one parameter is based on at least one of the at least one auditory test and the at least one auditory treatment procedure.

4. The practitioner device of claim 2, wherein the communication interface comprised in the practitioner device is configured for receiving at least one of the at least one sound signal, at least one parameter corresponding to the at least one sound signal, the result of the at least one auditory test, the at least one auditory test, the at least one auditory treatment procedure and a counselling protocol from the mobile device, wherein the at least one parameter is based on at least one of the at least one auditory test and the at least one auditory treatment procedure.

5. The practitioner device of claim 2, wherein the communication interface is configured for transmitting at least one of the at least one sound signal, at least one parameter corresponding to the at least one sound signal, the result of the at least one auditory test, the at least one auditory test, the at least one auditory treatment procedure and a counselling protocol to at least one of the mobile device and another practitioner device, wherein the at least one parameter is based on at least one of the at least one auditory test and the at least one auditory treatment procedure.

6. The practitioner device of claim 1, wherein the at least one auditory test is at least one of relative hearing loss test, tinnitus sound matching and capturing test, sound sensitivity disorder (SSD) test, hyperacusis test, misophonia test, insomnia test, stress test, depression test, hyperactivity test, anxiety test and relaxation test, wherein the at least one sound signal simulates an acoustic characteristic of a physical environment.

7. The practitioner device of claim 1, wherein the at least one auditory treatment procedure is at least one of Acoustic Tinnitus Masking Therapy (ATMT), Acoustic Tinnitus Retraining Therapy (ATRT), Acoustic Tinnitus Stimulation Therapy (ATST), Cognitive Habituation Tinnitus Therapy (CHaTT), Acoustic Insomnia Therapy (AIT), Acoustic Stress Therapy (AST), Acoustic Depression Therapy (ADT), Acoustic Hyperactivity Therapy (AHT), Acoustic Anxiety Therapy (AAT), and Acoustic Relaxation Therapy (ART), wherein the at least one auditory treatment procedure is based on at least one of habituation, suppression, distraction, attention diversion, relaxation, positive association and neuromodulation.

8. The practitioner device of claim 1 further comprising at least one sensor configured to sense at least one of sound perception for performing a Subjective Pure Tone Hearing Test, bone conduction for performing a Bone Conductive Hearing Test, Objective Acoustic Impedance, Auditory Brainstem Response and Auditory Steady-State Evoked Response.

9. The practitioner device of claim 1 further comprising an aural endoscope configured for capturing at least one image of at least a part of an ear.

10. The practitioner device of claim 1 further comprising at least one sensor configured for performing at least one of real-ear measurement and surround sound field assessment.

11. A method for facilitating at least one of testing and treatment of at least one auditory disorder, the method comprising:
 receiving, through a user interface of a practitioner device, an input from a practitioner; and
 communicating, through a communication interface of the practitioner device, information between the practitioner device and at least one of a mobile device and another practitioner device over at least one of a wired communication channel and a wireless communication channel, wherein the information is based on the input, wherein the information corresponds to at least one of at least one auditory test and at least one auditory treatment procedure, wherein the mobile device facilitates at least one of testing of at least one auditory disorder and treatment of at least one auditory disorder;
 the practitioner device comprising:
  a sound synthesizer configured for generating at least one sound signal, wherein the generating is in accordance with at least one parameter representing at least one of intensity, loudness, frequency, tone, bandwidth, noise, speech, rhythm, a start time, an end time and periodicity corresponding to the at least one sound signal;
  an audio port configured for interfacing with an acoustic transducer configured for generating acoustic waves based on the at least one sound signal, wherein a frequency of the acoustic waves is between 1 Hz and 20 KHz, wherein an intensity of the acoustic waves is between 0 dB and 120 dB;
  a controller configured for controlling at least one of the sound synthesizer and the audio port based on the information communicated by another practitioner device, wherein the controller is configured for performing at least one of the at least one auditory test and the at least one auditory treatment procedure in one of a synchronized mode and a desynchronized mode; and
  a storage module configured for storing at least one of the at least one sound signal, at least one parameter corresponding to the at least one sound signal, a result of the at least one auditory test and at least one auditory treatment and information corresponding to at least one of psychological training, education and counselling corresponding to the at least one auditory disorder, wherein the at least one parameter is based on at least one of the at least one auditory test and the at least one auditory treatment procedure.

12. The method of claim 11, wherein the mobile device comprises:
 the controller configured for controlling at least one of the sound synthesizer and the audio port based on the information communicated by the practitioner device.

13. The method of claim 12, wherein the information comprises at least one parameter, wherein the sound synthesizer is configured for generating the at least one sound signal in accordance with the at least one parameter, wherein the at least one parameter is based on at least one of the at least one auditory test and the at least one auditory treatment procedure.

14. The method of claim 12, wherein the communication interface comprised in the practitioner device is configured for receiving at least one of the at least one sound signal, at least one parameter corresponding to the at least one sound signal, the result of the at least one auditory test, the at least one auditory test, the at least one auditory treatment procedure and a counselling protocol from the mobile device, wherein the at least one parameter is based on at least one of the at least one auditory test and the at least one auditory treatment procedure.

15. The method of claim 12, wherein the communication interface is configured for transmitting at least one of the at least one sound signal, at least one parameter corresponding to the at least one sound signal, the result of the at least one auditory test, the at least one auditory test, the at least one auditory treatment procedure and a counselling protocol to at least one of the mobile device and another practitioner device, wherein the at least one parameter is based on at least one of the at least one auditory test and the at least one auditory treatment procedure.

16. The method of claim 11, wherein the at least one auditory test is at least one of relative hearing loss test, tinnitus sound matching and capturing test, sound sensitivity disorder (SSD) test, hyperacusis test, misophonia test, insomnia test, stress test, depression test, hyperactivity test, anxiety test, and relaxation test, wherein the at least one sound signal simulates an acoustic characteristic of a physical environment.

17. The method of claim 11, wherein the at least one auditory treatment procedure is at least one of Acoustic Tinnitus Masking Therapy (ATMT), Acoustic Tinnitus Retraining Therapy (ATRT), Acoustic Tinnitus Stimulation Therapy (ATST), Cognitive Habituation Tinnitus Therapy (CHaTT), Acoustic Insomnia Therapy (AIT), Acoustic Stress Therapy (AST), Acoustic Depression Therapy (ADT), Acoustic Hyperactivity Therapy (AHT), Acoustic Anxiety Therapy (AAT), and Acoustic Relaxation Therapy (ART), wherein the at least one auditory treatment procedure is based on at least one of habituation, suppression, distraction, attention diversion, relaxation, positive association and neuromodulation.

18. The method of claim 11 further comprising sensing, using at least one sensor, at least one of sound perception for performing a Subjective Pure Tone Hearing Test and bone conduction for performing a Bone Conductive Hearing Test, and Objective Acoustic Impedance, Auditory Brainstem Response and Auditory Steady-State Evoked Response.

19. The method of claim 11 further comprising:
 capturing, using an aural endoscope, at least one image of at least a part of an ear; and
 performing, using at least one sensor, at least one of real-ear measurement and surround sound field assessment.

20. The method of claim 11 further comprising billing a user for a service of providing at least one of the at least one auditory test, the at least one auditory treatment procedure, psychological training, education and counselling, wherein the billing is based on the service provided to the user.

* * * * *